US00PP18818P2

(12) United States Plant Patent
Leue

(10) Patent No.: US PP18,818 P2
(45) Date of Patent: May 20, 2008

(54) ***ANGELONIA* PLANT NAMED 'BALANGBAKIN'**

(50) Latin Name: *Angelonia angustifolia*
Varietal Denomination: Balangbakin

(75) Inventor: Ellen Leue, DeKalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 33 days.

(21) Appl. No.: 11/605,110

(22) Filed: Nov. 28, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

European Plant Breeders' Rights application No. 2006/2254 filed Nov. 8, 2006.

*Primary Examiner*—Kent Bell
*Assistant Examiner*—Louanne Krawczewicz Myers
(74) *Attorney, Agent, or Firm*—Audrey Charles

(57) ABSTRACT

A new and distinct cultivar of *Angelonia* plant named 'Balangbakin', characterized by its lavender pink-colored flowers, medium green-colored foliage, and moderately vigorous, prostrate growth habit.

1 Drawing Sheet

Latin name of genus and species of plant claimed: *Angelonia angustifolia.*
Variety denomination: 'Balangbakin'.

BACKGROUND OF THE INVENTION

The present invention relates to a new and distinct cultivar of *Angelonia* plant botanically known as *Angelonia angustifolia* and hereinafter referred to by the cultivar name 'Balangbakin'.

The new cultivar originated in a controlled breeding program in Elburn, Ill. during June 2003. The objective of the breeding program was the development of *Angelonia* cultivars with unique flower coloration, continuous flowering, and a moderately vigorous, freely branching, and prostrate growth habit.

The new cultivar is the result of cross-pollination. The female (seed) parent of the new cultivar is the proprietary *Angelonia angustifolia* breeding selection designated 147-1,2-6-2-3, not patented, characterized by white-colored flowers, dark green-colored foliage, and semi-prostrate growth habit. The male (pollen) parent of the new cultivar is AngelMist® Basket Purple 'Balangbeke', U.S. Plant Pat. No. 15,546, characterized by purple-colored flowers, medium green-colored foliage, and semi-prostrate to trailing growth habit. The new *Angelonia* cultivar was discovered and selected at a single flowering plant within the progeny of the above stated cross-pollination during March 2004 in a controlled environment at Elburn, Ill.

Asexual reproduction of the new cultivar by terminal stem cuttings since March 2004 at Elburn, Ill., Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balangbakin' as a new and distinct cultivar of *Angelonia* plant:

1. Lavender pink-colored flowers;
2. Medium green-colored foliage; and
3. Moderately vigorous, prostrate growth habit.

Plants of the new cultivar differ from plants of the female parent primarily in flower color, foliage color, and growth habit.

Of the many commercially available *Angelonia* cultivars known to the inventor, the most similar in comparison to the new cultivar is the male parent AngelMist® Basket Purple 'Balangbeke', U.S. Plant Pat. No. 15,546. However, in side by side comparisons, plants of the new cultivar differ from plants of 'Balangbeke' in the following characteristics:

1. Plants of the new cultivar have a flower color different from plants of 'Balangbeke'; and
2. Plants of the new cultivar are narrower than plants of 'Balangbeke'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balangbakin'. The plants were grown in 4.5 inch pots for 9 weeks in a greenhouse at West Chicago, Ill.

DETAILED BOTANICAL DESCRIPTION

Figure 1:
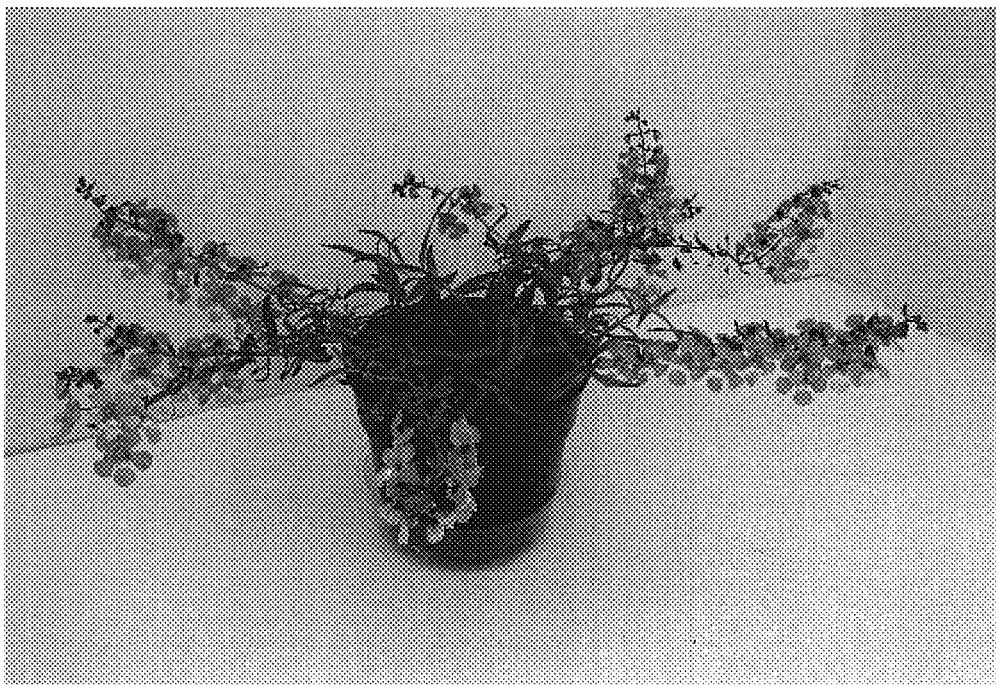
FIG. 1 illustrates a side view of the overall growth and flowering habit of 'Balangbakin'.
Figure 2:
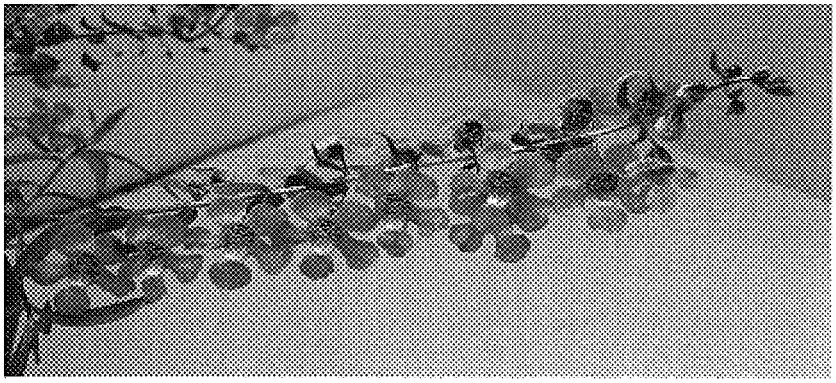
FIG. 2 illustrates a close-up view of an individual inflorescence of 'Balangbakin'.
Figure 3:
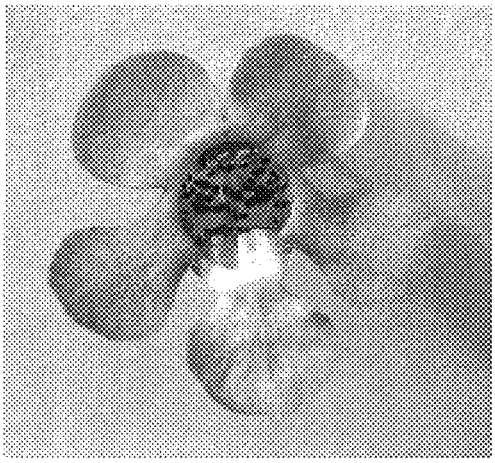
FIG. 3 illustrates a close-up view of an individual flower of 'Balangbakin'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Sep. 8, 2006 between 9:00 p.m. and 11:00 p.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 9 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Angelonia angustifolia* cultivar Balangbakin.

Parentage:

*Female parent.*—Proprietary *Angelonia angustifolia* breeding selection designated 147-1,2-6-2-3, not patented.

*Male parent.*—AngelMist Basket Purple 'Balangbeke', U.S. Plant Pat. No. 15,546.

Propagation:

*Type cutting.*—Terminal stem.

*Time to initiate roots.*—Approximately 7 to 9 days.

*Time to produce a rooted cutting.*—Approximately 24 to 28 days.

*Root description.*—Fine, fibrous.

*Rooting habit.*—Freely branching.

Plant description:

*Commercial crop time.*—Approximately 6 to 8 weeks from a rooted cutting.

*Growth habit and general appearance.*—Moderately vigorous, prostrate.

*Size.*—Height from soil level to top of plant plane: Approximately 15.9 cm. Width: Approximately 44.6 cm.

*Branching habit.*—Freely branching, pinching improves branching habit. Quantity of main branches per plant: Approximately 5.

*Branch.*—Shape: Square in cross section. Strength: Somewhat brittle. Length from soil level to base of raceme: Approximately 15.9 cm. Diameter: Approximately 2.6 mm. Length of central internode: Approximately 2.4 cm. Texture: Glabrous. Color of young and mature stems: 144B.

Foliage description:

*General description.*—Quantity of leaves per main branch: Approximately 16. Fragrance: None. Form: Simple. Arrangement: Opposite.

*Leaves.*—Aspect: Perpendicular or obtuse angle to stem. Shape: Elliptic. Margin: Widely serrate. Apex: Acute. Base: Sessile. Venation pattern: Pinnate. Length of mature leaf: Approximately 5.0 mm. Width of mature leaf: Approximately 7.8 mm. Texture of upper and lower surfaces: Glabrous. Color of upper surface of young and mature foliage: 137A with venation of 144B. Color of lower surface of young and mature foliage: 137C with venation of 144D.

Flowering description:

*Flowering habit.*—'Balangbakin' is freely flowering under outdoor growing conditions with substantially continuous blooming from spring through autumn and year-round in greenhouse environment.

*Lastingness of individual flower on the plant.*—Approximately 7 to 10 days.

Inflorescence description:

*General description.*—Type: Terminal raceme. Quantity per plant: Approximately 5. Fragrance: Slight, sweet. Length or height: Approximately 12.8 cm. Width: Approximately 4.2 cm. Quantity of fully open flowers per inflorescence: Approximately 12.

Flower description:

*Type.*—Solitary, zygomorphic.

*Bud.*—Rate of opening: Generally takes 3 to 4 days for bud to progress from first color to fully open flower.

*Bud just before opening.*—Shape: Globular. Length: Approximately 7.4 mm. Diameter: Approximately 7.4 mm. Color of upper surface: 75B with base of 75A. Color of lower surface: 144D with spots of N79A.

*Corolla.*—Shape: Bilabiate. Aspect: Facing outward. Length: Approximately 2.4 cm. Width: Approximately 2.3 cm. Depth: Approximately 5.8 mm.

*Petals.*—Quantity: 5, fused at base forming a throat and consisting of an upper lip with 2 petals and a lower lip with 3 petals consisting of 2 lateral petals and one central petal. Shape: Obovate. Margin: Entire. Apex: Obtuse.

*Upper lip.*—Length of petals from throat: Approximately 8.2 mm. Width of each petal: Approximately 1.0 cm. Texture of upper surface: Densely glandular pubescent. Gland color: Colorless, transparent. Texture of lower surface: Glabrous. Color of upper surface when fully open: N74D. Color of lower surface when fully open: 75A.

*Lower lip, lateral petals.*—Length of petals from throat: Approximately 9.1 mm. Width of each petal: Approximately 8.7 mm. Texture of upper and lower surfaces: Densely glandular pubescent. Gland color: Colorless, transparent. Color of upper surface when fully open: Closest to N74D with spots of N80B. Color of lower surface when fully open: 75A with a central spot of 75C.

*Lower lip, central petal.*—Length from palate: Approximately 7.2 mm. Width: Approximately 8.6 mm. Texture of upper and lower surfaces: Densely glandular pubescent. Gland color: Colorless, transparent. Color of upper surface when fully open: Lighter than N74D with spots of N80B. Color of lower surface when fully open: 75A at apex transitioning to 75D at base.

*Throat.*—Length: Approximately 8.1 mm. Width: Approximately: 6.1 mm. Texture of inner surface: Sparsely glandular pubescent. Gland color: Colorless, transparent. Texture of outer surface: Glabrous. Color of inner surface: 155D with spots and streaks of N79B. Color of outer surface: 75A with spots and streaks of N79B. Palate color: 155D with a central spot of N144D or two central streaks of N144D. Palate texture: Glabrous with glandular pubescent margin. Gland color: 150C, transparent. Teeth color: 155D.

*Calyx.*—Shape: Star, cupped. Diameter: Approximately 6.0 mm.

*Sepals.*—Quantity per flower: 5. Shape: Lanceolate. Apex: Acute. Base: Fused. Margin: Entire. Length: Approximately 3.0 mm. Width: Approximately 1.0 mm. Texture of upper surface: Glabrous. Texture of lower surface: Glandular pubescent at base. Gland color: Colorless, transparent. Color of upper surface: 146B with margin and base of 187A. Color of lower surface: 146B with a strong overlay of 187A.

*Pedicel.*—Strength: Strong, flexible. Aspect: Primarily perpendicular to stem. Length: Approximately 9.5 mm. Diameter: Less than 1 mm. Texture: Glabrous. Color: 187A.

*Reproductive organs.*—Androecium: Stamen quantity: 4 per flower. Stamen length: 4 mm. Filament length: Approximately 3.0 mm. Filament color: 84D. Anther shape: Bilobed. Anther length: Approximately 1.0 mm. Anther color: 84C. Pollen amount: Sparse. Pollen color: 155D. Gynoecium: Pistil quantity: 1 per flower. Pistil length: Approximately 4.0 mm. Stigma shape: Pointed. Stigma length: Less than 1 mm. Stigma color: Colorless, opaque. Style length: Approximately 3.0 mm. Style color: Purer white than 155D with streaks of 84A near stigma. Ovary diameter: Approximately 1.0 mm. Ovary texture: Glabrous. Ovary color: 146D with spots of 187A.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balangbakin', substantially as herein shown and described.

* * * * *